United States Patent [19]

Shibata

[11] Patent Number: 4,946,577
[45] Date of Patent: Aug. 7, 1990

[54] OXYGEN SENSOR

[75] Inventor: Kazuyoshi Shibata, Nagoya, Japan

[73] Assignee: NGK Insulators, Ltd., Japan

[21] Appl. No.: 417,032

[22] Filed: Oct. 4, 1989

[30] Foreign Application Priority Data

Oct. 4, 1988 [JP] Japan .................................. 63-250627

[51] Int. Cl.$^5$ ............................................ G01N 27/409
[52] U.S. Cl. ..................................... 204/427; 204/424
[58] Field of Search ................ 204/421, 422, 423, 424, 204/425, 426, 427, 428, 429, 1 S

[56] References Cited

U.S. PATENT DOCUMENTS

| | | | |
|---|---|---|---|
| 3,843,400 | 10/1974 | Radford et al. | 204/421 X R |
| 4,514,277 | 4/1985 | Sakurai et al. | 204/424 |
| 4,584,086 | 4/1986 | Hayakawa et al. | 204/429 |
| 4,655,892 | 4/1987 | Satta et al. | 204/192.15 |

FOREIGN PATENT DOCUMENTS 50650 3/1982 Japan .

Primary Examiner—G. L. Kaplan
Attorney, Agent, or Firm—Arnold, White & Durkee

[57] ABSTRACT

An oxygen sensor having an oxygen sensing element which includes a solid electrolyte body made of an oxygen-ion conductive solid electrolyte material, and a measuring electrode and a reference electrode formed on the solid electrolyte body, the measuring and reference electrodes, respectively, communicating with a measurement gas and a reference gas having a predetermined oxygen concentration, so that an electromotive force is induced between the measuring and reference electrodes, based on a difference in oxygen concentration between the measurement gas and the reference gas. The measuring electrode includes a conductor principally consisting of platinum, and lead and/or zinc serving as an activation component for the platinum. An amount of the lead and/or zinc per 1 mg of the platinum is within a range of 0.2–100 μg.

6 Claims, 1 Drawing Sheet

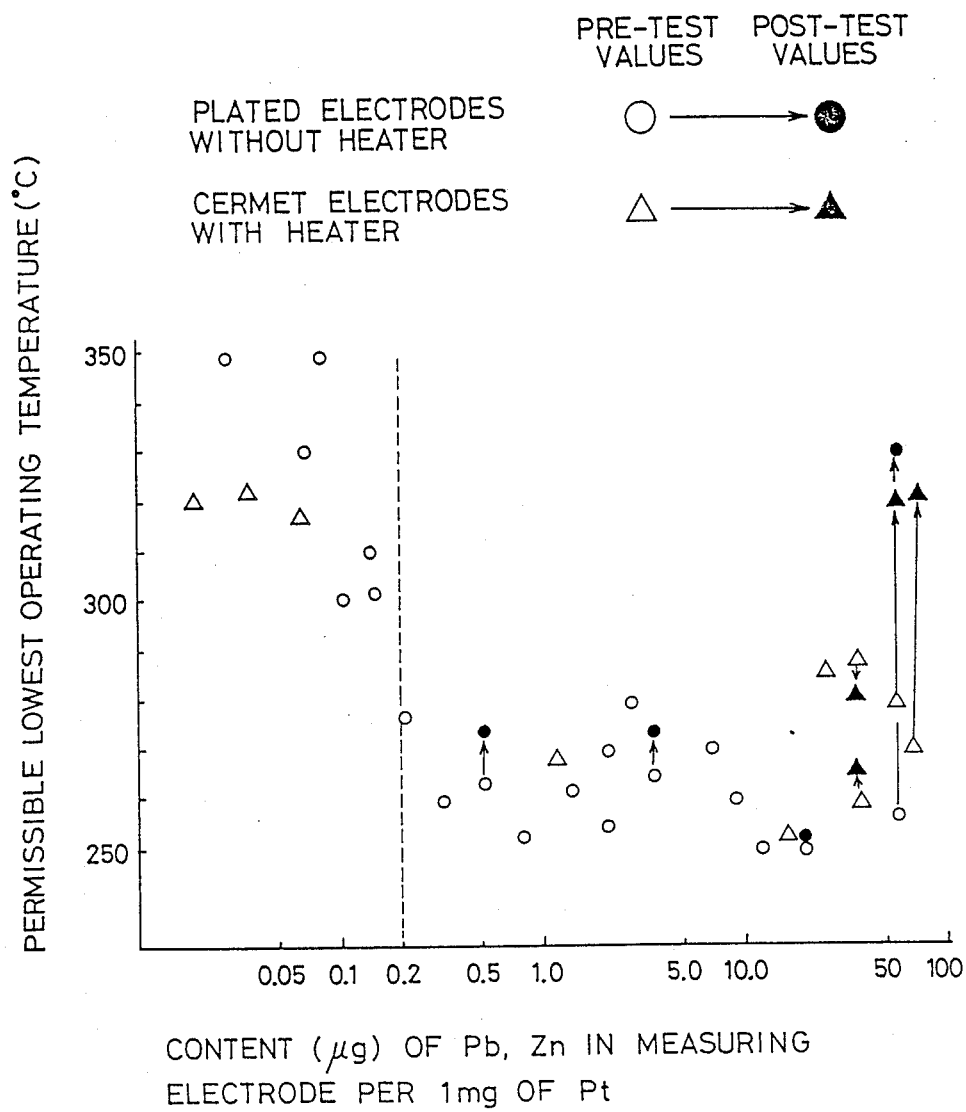

OXYGEN SENSOR

BACKGROUND OF THE INVENTION

1. Field of the Invention

The present invention relates in general to an oxygen sensor having an oxygen sensing element for determining an oxygen concentration in exhaust gases such as those emitted by internal combustion engines and boilers. More particularly, the invention is concerned with techniques useful for assuring a high operating response of the oxygen sensor at a relatively low temperature, and for minimizing a variation in the output characteristic of the sensor during its use.

2. Discussion of the Prior Art

It is known to use zirconia ceramics or other oxygen-ion conductive solid electrolyte materials, for determining an oxygen concentration in measurement gases such as exhaust gases produced by internal combustion engines of motor vehicles, or boilers, according to the principle of an oxygen concentration cell. Based on the determined oxygen concentration, an air/fuel ratio of an air-fuel mixture supplied to the engines or boilers is controlled to assure an optimum combustion or burning condition of the engines or boilers.

An oxygen sensor or detector for determining an oxygen concentration as indicated above includes a sensing element which uses a suitably shaped tubular or planar solid electrolyte body made of an oxygen-ion conductive solid electrolyte material. On the inner and outer surfaces of the solid electrolyte body, there are formed a pair of electrodes, respectively. One of the electrodes which is formed on the inner surface communicates with an ambient air or atmosphere so that it functions as a reference electrode exposed to the ambient air, which serves as a reference gas having a reference oxygen concentration. The other electrode formed on the outer surface of the solid electrolyte body communicates with exhaust gases so that it functions as a measuring electrode exposed to the exhaust gases, i.e., a measurement gas to be measured. The sensing element is adapted to detect an electromotive force which is induced between the reference and measuring electrodes, due to a difference in the oxygen concentration between the atmospheres to which the two electrodes are exposed. Thus, the oxygen concentration in the exhaust gases is determined.

The oxygen sensor of the type described above is required to operate with sufficient reliability over a relatively wide temperature range, for determining the oxygen concentration in the exhaust gases whose temperature varies to a considerably large extent. However, the output of the oxygen sensor tends to be unstable or unreliable when the temperature of the exhaust gases is relatively low, since the function of the electrodes as a catalyst is deteriorated at a low temperature. Thus, the known oxygen sensor is not capable of accurately detecting the oxygen concentration of the exhaust gases, when the temperature of the exhaust gases at the detecting portion of the sensor is lower than 300° C.-350° C.

As one type of electrode used in the oxygen sensor, there is known an electrode formed of a cermet which is a mixture of catalytic metal powder and ceramic powder. The cermet electrode is formed on a solid electrolyte body formed of an oxygen-ion conductive solid electrolyte material such as fully or partially stabilized zirconia, by applying a paste of the cermet to the surface of the fired solid electrolyte body and firing the applied cermet paste, or by co-firing the cermet with a green sheet of the solid electrolyte body to which the cermet has been applied. Thus, an oxygen sensing element with the cermet electrode formed on the solid electrolyte body is prepared. This cermet electrode is advantageous in its improved durability or prolonged life expectancy, even when used under severe operating conditions such as a considerably high temperature.

For assuring the improved durability of the cermet electrode, the cermet material applied to the fired or unfired solid electrolyte body must be baked or fired at a high temperature of not lower than 1000° C., more preferably, 1300° C. or higher. As a result, the activity of the cermet electrode as a catalyst is significantly deteriorated, and therefore the application of the oxygen sensing element is unfavorably limited.

To alleviate the problems encountered in the cermet electrode, and other types of electrodes such as an electrode formed by plating, it has been proposed to provide the oxygen sensor with a heater for heating the sensing element, more particularly, a portion of the element on which the electrodes are formed, so that that portion of the sensing element is maintained at an optimum operating temperature even when the temperature of the exhaust gases is low. In this heater-built-in oxygen sensor, however, the measuring electrode which is exposed to the measurement gas (exhaust gases) is cooled by the measurement gas, when the temperature of the gas is relatively low. Accordingly, there still remains the problem of operating reliability or stability of the sensor output as described above.

In recent years, the exhaust gases emitted by the internal combustion engine of a motor vehicle have been strictly regulated for the protection of the environment. In order to keep pace with this tendency toward strict regulation of the engine emissions, there is a growing need for providing an automotive oxygen sensor operable during an idling operation of the engine, or an oxygen sensor operable in a reliable manner even when the sensor is installed in a low-temperature portion of an exhaust pipe remote from the engine because of limited installation space, for example, Nevertheless, the conventional oxygen sensor is unsatisfactory in its operating reliability, when the sensor is exposed to the low-temperature exhaust gases, for example, those having a temperature of lower than 300° C.

In the oxygen sensor of the type described above, it is recognized that the output characteristic of the sensor varies during a relatively short initial period of use, due to an initial aging phenomenon, so-called "green effect". More specifically, the operating characteristic of the sensing element is improved with an increase of a cumulative operating time, i.e., cumulative time of exposure to exhaust gases, due to deposition of some components contained in the exhaust gases on the measuring electrode, or due to a change (usually, an improvement) in the catalytic activity of the measuring electrode. For reducing the variation in the output characteristic and sensing accuracy of the sensor, it is desirable to eliminate or reduce this "green effect" which occurs during the initial period of use. In other words, as the cumulative operating time of the sensing element of the oxygen sensor increases, the air/fuel ratio represented by the sensor output tends to be lowered as compared with that detected when the sensor is initially used.

SUMMARY OF THE INVENTION

The present invention was developed in light of the above problems experienced in the prior art. It is accordingly an object of the present invention to provide an oxygen sensor which operates in a reliable manner even when the temperature of the measurement gas is relatively low, and which is substantially free of the "green effect" which occurs during an initial time of use, thereby assuring an improved sensing accuracy.

The above object may be attained according to the principle of the invention, which provides an oxygen sensor having an oxygen sensing element which includes a solid electrolyte body made of an oxygen-ion conductive solid electrolyte material, and a measuring electrode and a reference electrode formed on the solid electrolyte body. The measuring and reference electrodes, respectively, communicate with a measurement gas, and a reference gas having a predetermined oxygen concentration, so that an electromotive force is induced between the measuring and reference electrodes, based on a difference in oxygen concentration between the measurement gas and the reference gas. The improvement comprises the measuring electrode including a conductor principally consisting of platinum, and lead and/or zinc serving as an activation component for the platinum, an amount of lead and/or zinc per 1 mg of platinum being within a range of 0.2-100 $\mu$g.

Preferably, the measuring electrode includes lead and/or zinc in a maximum amount of 50 $\mu$g per 1 mg of platinum. Further, it is desirable that the measuring electrode is formed of a cermet layer which includes platinum as a major conductive metallic component, and a ceramic material.

It is also preferable that the measuring electrode is covered by a porous ceramic protective layer formed of a ceramic material. In this case, it is desirable that lead and/or zinc included in the measuring electrode be uniformly distributed in the direction of thickness of the electrode.

Moreover, the instant oxygen sensor may advantageously comprise a heater for heating at least a portion of the oxygen sensing element on which the measuring electrode is formed.

In the oxygen sensing element of the oxygen sensor constructed as described above, the measuring electrode formed on the solid electrolyte body made of the oxygen-ion conductive solid electrolyte material includes the conductor principally consisting of platinum, and a suitable amount of lead and/or zinc for a given amount of platinum for activating the platinum measuring electrode which serves as a catalyst. This permits the measuring electrode to effectively operate even when exposed to the low-temperature measurement gas. Accordingly, the instant oxygen sensor is able to exhibit improved consistency of output characteristics; that is, produce an output which accurately represents the oxygen concentration in the measurement gas.

The above-indicated suitable amount of lead and/or zinc contained in the measuring electrode is generally 0.2-100 $\mu$g, more preferably, not exceeding 50 $\mu$g, per 1 mg of platinum of the measuring electrode. If the amount of lead and/or zinc per 1 mg of platinum is less than 0.2 $\mu$g, the output of the oxygen sensor becomes greatly unreliable. Particularly, when a large number of oxygen sensors are manufactured with the measuring electrode of each sensor containing approximately 0.1 $\mu$g of lead and/or zinc per 1 mg of platinum, the individual oxygen sensors vary to a great extent in terms of the sensing characteristics such as a catalytic activation property. It follows from the above description that the oxygen sensor is stabilized in its operating characteristics when the measuring electrode is impregnated with 0.2 $\mu$g or larger amount of lead and/or zinc per 1 mg of platinum.

If the amount of lead and/or zinc contained in the measuring electrode exceeds 100 $\mu$g per 1 mg of platinum, the oxygen sensor may suffer from insufficient durability of the measuring electrode due to weak adhesion to the solid electrolyte body, or accelerated consumption of the measuring electrode due to exposure to the high-temperature exhaust gases. Further, the electrode material containing the above-indicated amount of lead and/or zinc may be less durable during the sintering process thereof. While the degree of deterioration of the measurement electrode as described above varies from one oxygen sensing element to another, it is preferable that the lead and/or zinc amount contained in the measuring electrode which is used under comparatively severe conditions is no more than 50 $\mu$g per 1 mg of platinum.

To sum up, the oxygen sensor of the present invention is adapted such that a specific amount of lead and/or zinc is contained in the platinum measuring electrode, whereby the operating reliability of the sensor at a relatively low temperature is significantly improved; that is, reliable sensor outputs can be obtained by the instant oxygen sensor even when the temperature of the measurement gas is relatively low. The reliability of the oxygen sensor as described above is further enhanced when the measuring electrode is formed of a cermet layer. Further, when the oxygen sensor is provided with a heater for heating a portion of the oxygen sensing element on which the measuring electrode is formed, the instant oxygen sensor is suited for use over a still wider temperature range of the measurement gas, with further improved properties of the measuring electrode. Thus, the provision of the heater is effective to further enhance the advantageous features of the present invention as described above.

The oxygen sensor constructed according to the present invention is also adapted such that the air/fuel ratio represented by the sensor output is preliminarily shifted toward a lower value, as compared with that detected by the conventional oxygen sensor during the initial period of use. In other words, the oxygen sensor is made substantially free of the "green effect" which would otherwise take place during the initial period of use.

BRIEF DESCRIPTION OF THE DRAWING

The above and optional objects, features and advantages of the present invention will become more apparent by reading the following detailed description of the invention, when considered in connection with the accompanying drawing, wherein the single FIGURE is a graph showing a relationship between a lead and/or zinc content of a measuring electrode of an oxygen sensor of the present invention, and the lowest permissible operating temperature of the oxygen sensor.

DETAILED DESCRIPTION OF THE INVENTION

The oxygen-ion conductive solid electrolyte for the solid electrolyte body (as a main body of the oxygen sensing element of the oxygen sensor) can be selected from among various known solid electrolyte materials, but is preferably formed of a fully or partially stabilized zirconia which includes a suitable stabilizing agent such as yttria ($Y_2O_3$), calcia (CaO), magnesia (MgO) or ytterbia ($Yb_2O_3$). Further, the solid electrolyte is mixed with a suitable sintering aid, for example, clay, such as kaolin, or $SiO_2$, $Al_2O_3$, $Fe_2O_3$.

The selected solid electrolyte material containing the sintering aid is formed into an unfired body having a desired shape, by a known technique such as a press molding process by using a rubber press, or a lamination process such as a thick-film forming method. As described below, the thus prepared unfired formed body gives, by firing thereof, the fired solid electrolyte body having a tubular or planar, or other desired configuration, which constitutes a main body of the oxygen sensing element.

Then, the unfired formed body may be calcined as needed, at a temperature lower than the firing temperature. The calcined or non-calcined formed body is fired in an ordinary known manner. On the surface of the unfired formed body or the fired solid electrolyte body, there are formed at least a measuring electrode and a reference electrode, which are exposed to the measurement gas (exhaust gases) and the reference gas, respectively.

These electrodes are thin layers formed of an electrically conductive material which consists of, or includes as a major component, a metal of the platinum group, such as platinum, ruthenium, osmium, iridium, rhodium and palladium. Particularly, the measuring electrode is formed of a conductor which includes platinum as a major component. For example, the measuring electrode is formed of a metal conductor which consists solely of platinum, or which includes approximately 1-30% of another metal, such as rhodium or palladium, in addition to platinum used as the major component.

The formation of the electrodes as described above is effected by one of various known methods, for example: plating; sputtering; thermal decomposition of a salt of selected metal; or firing or baking of a cermet paste which is formed of the selected metal and ceramic and is applied to the surface of the fired solid electrolyte body. Alternatively, the electrode may be formed by applying such a cermet paste to a green sheet of the solid electrolyte body, and then co-firing the cermet paste and the green sheet of the solid electrolyte body.

To improve the adhesion of the electrodes to the solid electrolyte body, and thereby enhance the properties of the electrodes, it is advantageous to effect etching on the surface of the solid electrolyte body prior to forming the electrodes by plating, sputtering or other method, so that the electrodes are formed on the etched portions of the solid electrolyte body.

The cermet paste which gives the cermet electrode is generally prepared by mixing a powder of catalytic metal selected from the platinum group as described above, with a powder of the oxygen-ion conductive solid electrolyte material as used for the solid electrolyte body. The catalytic metal powder may be a platinum powder, or a mixture of the platinum powder and a powder of the other platinum group metal. The solid electrolyte powder for the cermet paste may be replaced by a ceramic powder such as alumina. The thus prepared cermet paste is applied by printing or brushing to the surface of an unfired formed body made of a solid electrolyte material, and then is co-fired with the unfired formed body, whereby the fired solid electrolyte body having the cermet electrode formed thereon is prepared, with an extremely large force of adhesion between the co-fired solid electrolyte body and electrode.

After the reference and measuring electrodes are formed on the solid electrolyte body in the manner as described above, the measuring electrode may be covered as needed, by a porous ceramic protective overcoat having a suitable thickness, in order to increase the durability of the measuring electrode. This ceramic protective overcoat can be formed by various known methods, for example by applying a ceramic material, such as spinel ($Al_2O_3 \bullet MgO$), zirconia, or alumina, over the measuring electrode, by a plasma or flame spraying method. Alternatively, a powder of the ceramic material as described above is processed into a slurry, so that the ceramic protective overcoat is formed by applying the obtained ceramic slurry by printing over the measuring electrode, or by dipping the measuring electrode in the ceramic slurry. Then, the slurry applied to the electrode is fired. It is also possible that the ceramic slurry is applied to the cermet paste for the measuring electrode, and is then co-fired with the cermet paste, to obtain the cermet electrode coated by the protective overcoat.

In the oxygen sensor according to the present invention, the measuring electrode of the oxygen sensing element contains a specific amount of lead and/or zinc. The specific amount of lead, zinc, or a compound thereof may be included in a selected electrode material which is subsequently applied to the solid electrolyte body to form the measuring electrode. In this case, the addition of lead and/or zinc is completed when the measuring electrode is formed on the body. Alternatively, the measuring electrode already formed on the solid electrolyte body may be impregnated or doped with lead, zinc, or a compound thereof, by applying such a material to the measuring electrode formed on the solid electrolyte body, and then effecting a suitable heat treatment. Usually, this heat treatment is favorably carried out under a reducing atmosphere, such as CO or $H_2$ gas.

The thus obtained oxygen sensing element wherein the measuring electrode contains a specific amount of lead and/or zinc as described above is capable of operating in a reliable manner even when the temperature of the measurement gas is relatively low. Further, this sensing element has a reduced variation in the output characteristics during an initial period of use. Namely, the air/fuel ratio represented by the output of the sensing element provided with the instant measuring electrode does not considerably suffer from a variation due to the conventionally experienced "green effect", that is, the air/fuel ratio at the very beginning of use of the instant sensor is almost equal to that detected by the conventional sensor which has been aged in a certain period after the start of use. Hence, the sensing element having these features is advantageously installed on the instant oxygen sensor.

EXAMPLES

To further clarify the concept of the present invention, some specific examples embodying the invention will be described with a certain degree of particularly. However, it is to be understood that the invention is by no means limited to the precise details of the illustrated examples.

It is further to be understood that the present invention may be embodied with various changes, modifications and improvements, which may occur to those skilled in the art, without departing from the spirit and scope of the invention.

Initially, a solid electrolyte material consisting of 94 mole % of zirconia and 6 mole % of yttria was calcined for an hour at 1200° C., and then mixed with a sintering aid of 5% by weight of $Al_2O_3$ and 0.5% by weight of $SiO_2$. The obtained mixture was wet-ground with almina balls, for 30 hours in a ball mill, and then a binder was added to the ground powder. Subsequently, the obtained mass was processed by a spray drier, so as to prepare a solid electrolyte material in the form of granules whose grain size was about 50 μm.

By using the thus prepared granular solid electrolyte material, unfired tubular bodies for oxygen sensing elements having an ordinary known configuration were formed by a rubber press. Then, the outer circumferential surface of each unfired tubular body was sliced so that the unfired bodies have a predetermined configuration. The thus suitably shaped unfired bodies were fired for two hours at 1300° C. so as to obtain main bodies of oxygen sensing elements, which were made of an oxygen-ion conductive solid electrolyte.

Subsequently, reference and measuring electrodes each having a suitable thickness were formed on the inner and outer surfaces of each fired solid electrolyte body, by either of the following two methods: (a) applying platinum to the solid electrolyte body by an ordinary plating method; or (b) applying a platinum paste to the solid electrolyte body, and firing the applied paste on the body. Successively, a ceramic material whose major component consists of spinel was applied by a plasma-spraying method to the surface of the measuring electrode of each solid electrolyte body, whereby a porous protective overcoat having a thickness of about 100 μm was formed. Then, the measuring electrodes of the sensing elements were impregnated or doped with lead and/or zinc by respective methods specified in Table 1. Hence, six groups of oxygen sensing elements (1-1, 1-2, . . . 1-6) were prepared, each group consisting of five specimens.

TABLE 1

| Sensing element | Measuring electrode (thickness) | Catalytic activation compound | Method for introducing lead and/or zinc |
|---|---|---|---|
| 1-1 | Pt-plated electrode (0.7 μm) | $PbCl_2$ aqueous solution (0.5 g/l) | Dipping and heat treatment 350° C. × 1 Hr under $H_2$ gas |
| 1-2 | Pt-plated electrode (0.7 μm) | $PbCl_2$ aqueous solution (1 g/l) | Dipping and heat treatment 870° C. × 1 Hr under atmosphere |
| 1-3 | Pt-plated electrode (1.0 μm) | PbO powder (0.5 mg/element) | Heat treatment under slight air stream 500° C. × 30 Hr containing PbO vapor |
| 1-4 | Pt-plated electrode (1.5 μm) | PbO powder (1 mg/element) | Heat treatment under CO gas stream 850° C. × 10 Hr containing Pb vapor |
| 1-5 | Pt-plated electrode (1.5 μm) | $(CH_3COO)_2Zn$ aqueous solution (1 g/l) | Dipping and heat treatment 500° C. × 1 Hr under atmosphere |
| 1-6 | Electrode formed from Pt paste | Adding Pb into Pt paste (10 μg/mg · Pt) | Firing Pt paste on the solid electrolyte body 950° C. × 5 min. |

Each of the thus prepared oxygen sensing elements in which the measuring electrode contains lead and/or zinc was built in a metal casing, as in the known oxygen sensor. The sensing elements were tested for their operating responses.

Instead of the platinum electrodes formed on the fired solid electrolyte bodies as described above, cermet electrodes were formed on solid electrolyte bodies made of the same oxygen-ion conductive solid electrolyte material as described above. More specifically described, a cermet paste was prepared by adding 30 parts by weight of a powder of the same solid electrolyte material as used for the solid electrolyte bodies, to 100 parts by weight of a metallic powdered mixture consisting of 90% by weight of platinum and 10% by weight of rhodium. The thus prepared cermet paste was applied to appropriate portions of the inner and outer surfaces of each unfired tubular body made of the above-described granular solid electrolyte material. Then, a porous protective layer made of zirconia was formed over the cermet paste applied to the outer surface of each unfired tubular body. These unfired tubular bodies, cermet paste, and porous protective layers were co-fired to give some specimens of an oxygen sensing element.

Then, the measuring electrodes of the thus obtained sensing elements were impregnated with a certain amount of lead and/or zinc by respective methods as specified in Table 2.

TABLE 2

| Sensing element | Measuring Electrode | Catalytic activation composition | Method for introducing lead and/or zinc |
|---|---|---|---|
| 2-1 | Cermet electrode (Pt/Rh = 90/10) /$ZrO_2$ = 100/30 | $ZnCl_2$ powder (1 mg/element) | Exposed to $ZnCl_2$ vapor stream at 400° C. for 15 min. (vaporized $ZnCl_2$ powder) |
| 2-2 | | powdered glass containing 50% Pb (0.5 mg/element) | Treating sensing element under CO gas at 850° C. for 10 Hr (vaporized catalytic activation compound) |
| 2-3 | | Zn/Pb = 1/1 mixed metallic powder (0.8 mg/element) | Treating sensing element under $H_2$ gas at 450° C. for 1 Hr (vaporized metallic powder) |

Hence, three groups of sensing elements (2-1, 2-2 and 2-3) were prepared, each consisting of five specimens.

Each of the thus prepared oxygen sensing elements was built in a metal casing as in the ordinary oxygen sensor. The sensing elements were tested for their operating responses. Each of the oxygen sensors having the specimens was provided with a rod-like ceramic heater, which was disposed in the inner bore of the tubular solid electrolyte body, as is well known in the art.

TESTING METHOD

Oxygen sensors were prepared by using the above-described speciments (1-1, 1-2, . . . 2-3) of the oxygen sensing element. The sensors were attached to an exhaust pipe of a four cylinder EFI gasoline engine (having an electronic fuel injector, and a 1.5 l displacement), such that the sensing elements were exposed to exhaust gases emitted by the engine. After the engine was warmed up for 10 minutes as the temperature of the exhaust gases was raised to 400° C., the engine speed was lowered to 800 rpm, and an A/F ratio of an air/fuel mixture supplied to the engine was periodically changed between 14.0 and 15.3 at the interval of 3 seconds. It was recognized that as the temperature of the exhaust gases fell, the amplitude of voltage output waveform produced by the oxygen sensors was reduced. In this condition, the temperature of the exhaust gases was measured when the amplitude of the output of each oxygen sensor was reduced to 0.5 V. The measured temperature was determined to be a permissible lowest operating temperature of the relevant oxygen sensor.

The oxygen sensing elements were also tested in terms of the initial aging during an initial time of use. This test was conducted in the following manner. Oxygen sensors having the sensing elements of the groups 1-1 through 1-6 (Table 1) were installed in the exhaust pipe of the engine similar to that used for the above test, such that the detecting portion of each sensing element was exposed to exhaust gases. With the temperature of the exhaust gases maintained at 350° C., the sensor output produced by each oxygen sensor was measured while the A/F ratio of the air-fuel mixture supplied to the engine was changed from 13.5 to 16.5. The A/F ratio (or excess air ratio $\lambda s = {}^{A/F}/14.7$) obtained at the sensor output of 0.5 V was used to estimate the effect of aging of the relevant sensing element on its output during an initial time of use.

TEST RESULTS (1) The test revealed that the permissible lowest operating temperature of all of the five specimens (n=5) of the five groups 1-1, 1-2, . . . 1-5 as indicated in Table 1 was 280° C. or lower, while that of a comparative example of an oxygen sensing element whose Pt-plated measuring electrode has no lead and/or zinc was 330° C. It follows from this result that the addition of lead and/or zinc into the measuring electrode of an oxygen sensing element is effective to enhance the sensing accuracy of the sensing element when used at a relatively low temperature. In the test, the distributions of lead or zinc and platinum in the measuring electrodes of the above five groups of sensing elements were observed by means of a quantitative analysis as is well known in the art. This analysis revealed that the amounts of lead or zinc which appeared in respective effective detecting portions of these measuring electrodes (which portions were exposed to the measurement gas so as to actually detect the oxygen concentration of the gas) were within a range of 0.2–60 µg per 1 mg of platinum.

(2) The same test revealed that the permissible lowest operating temperature of all of the specimens (n=5) of the group 1-6 was 280° C. or lower, while that of a comparative example whose measuring electrode has no lead and/or zinc was 350° C. The quantitative analysis of these specimens revealed that the amounts of lead at respective effective detecting portions of the measuring electrodes were within a range of 2–4 µg per 1 mg of platinum.

(3) The same test also revealed that the permissible lowest operating temperature of all of the specimens (n=5) of the three groups 2-1, 2-2 and 2-3, as indicated in Table 2, was 290° C. or lower, while that of a comparative specimen with no lead and/or zinc contained in the cermet electrode was 320° C., when the specimens were heated by the heater whose heat generating portion was maintained at 400° C. It follows that the sensing element of the oxygen sensor according to the present invention has significantly improved operating characteristics even when used at a relatively low temperature. The quantitative analysis of the specimens in the groups 2-1 through 2-3 revealed that the amounts of lead or zinc at respective effective detecting portions of the cermet measuring electrodes were within a range of 1–70 µg per 1 mg of platinum. On the other hand, the amount of lead and/or zinc at the same portion of the comparative specimen was no more than 0.1 µg/mg•Pt.

(4) The test for observing the effect of aging of the sensing elements revealed that the excess air ratios λs obtained at the sensor output of 0.5 V with respect to the sensing elements of the groups 1-1 through 1-6 were 1.01 or lower, while those obtained with respect to the comparative examples as described above were about 1.03–1.06. This means that the air/fuel ratio represented by the output of the oxygen sensor of the invention is lower than that of the conventional sensor, and will no longer be lowered considerably due to the aging of the measuring electrode.

COMPARATIVE EXAMPLE

As a comparative example, there was prepared a sample of an oxygen sensing element similar to the sensing elements of Group 1-2, which was chemically treated such that the Pt-plated electrode was dipped in an HCl aqueous solution in which the $PbCl_2$ content is 0.2g/l. The permissible lowest operating temperature of this comparative example was 300–310° C. The amount of lead included at the detecting portion of the Pt-plated electrode was 0.1–0.15 µg per 1 mg of platinum.

DURABILITY TEST

Oxygen sensors were prepared as described above by using various oxygen sensing elements which have respective measuring electrodes having different amounts of lead or zinc per 1 mg of platinum. The sensors were attached to an exhaust pipe of a gasoline engine having a 2 l displacement. The durability test was conducted such that the sensing elements were continuously exposed to exhaust gases of 1000° C. for 200 hours. The accompanying drawing shows a relationship between the permissible lowest operating temperature of each oxygen sensor before and after the durability test, and the amount of the lead and/or zinc contained per 1 mg of platinum of the measuring electrode used in the sensor. The drawing also shows the permissible lowest operating temperatures of other oxygen sensors using the specimens of the groups (1-1 through 2-3) and the comparative examples as described above.

It follows from the drawing that the amount of lead and/or zinc per 1 mg of platinum of the measuring electrode should not exceed 50 µg, so as to prevent a large variation in the lowest operating temperature of the sensor during a long period of service.

What is claimed is:

1. An oxygen sensor having an oxygen sensing element which includes a solid electrolyte body made of an oxygen-ion conductive solid electrolyte material, and a measuring electrode and a reference electrode formed on said solid electrolyte body, said measuring electrode and said reference electrode, respectively, communicating with a measurement gas and a reference gas having a predetermined oxygen concentration, so that an electromotive force is induced between said measuring electrode and said reference electrode, based on a difference in oxygen concentration between the measurement gas and the reference gas, wherein the improvement comprises:

said measuring electrode including a conductor principally consisting of platinum, and lead and/or zinc serving as an activation component for said platinum, an amount of said lead and/or zinc per 1 mg of said platinum being within a range of 0.2-100 $\mu$g.

2. An oxygen sensor according to claim 1, wherein the amount of said lead and/or zinc per 1 mg of said platinum is less than 50 $\mu$g.

3. An oxygen sensor according to claim 1, wherein said measuring electrode is formed of a cermet layer which includes platinum as a major conductive metallic component, and a ceramic material.

4. An oxygen sensor according to claim 3, wherein said ceramic material of said cermet layer includes said oxygen-ion conductive solid electrolyte material used for said solid electrolyte body.

5. An oxygen sensor according to claim 1, further comprising a heater for heating at least a portion of said oxygen sensing element on which said measuring electrode is formed.

6. An oxygen sensor according to claim 1, wherein said conductor of said measuring electrode includes a metal of the platinum group other than platinum, in addition to said platinum as a major component.

* * * * *